(12) United States Patent
Branton et al.

(10) Patent No.: US 8,470,408 B2
(45) Date of Patent: *Jun. 25, 2013

(54) CARBON NANOTUBE SYNTHESIS FOR NANOPORE DEVICES

(75) Inventors: Daniel Branton, Lexington, MA (US); Jene A. Golovchenko, Lexington, MA (US); Slaven Garaj, Cambridge, MA (US); Dimitar M. Vlassarev, Cambridge, MA (US); El-Hadi S. Sadki, Abu Dhabi (AE)

(73) Assignee: President and Fellows of Harvard College, Cambridge, MA (US)

( * ) Notice: Subject to any disclaimer, the term of this patent is extended or adjusted under 35 U.S.C. 154(b) by 1203 days.

This patent is subject to a terminal disclaimer.

(21) Appl. No.: 12/286,849

(22) Filed: Oct. 2, 2008

(65) Prior Publication Data
US 2009/0136682 A1    May 28, 2009

Related U.S. Application Data

(60) Provisional application No. 60/997,297, filed on Oct. 2, 2007.

(51) Int. Cl.
*D01F 9/12* (2006.01)
*C40B 50/14* (2006.01)
*C23C 16/00* (2006.01)
*B05D 3/00* (2006.01)

(52) U.S. Cl.
USPC ............ 427/532; 977/742; 977/843; 977/762

(58) Field of Classification Search
USPC ..................... 427/532; 977/762; 216/19, 39
See application file for complete search history.

(56) References Cited

U.S. PATENT DOCUMENTS 6,333,016 B1    12/2001    Resasco et al.
6,346,189 B1    2/2002     Dai et al.
(Continued)

FOREIGN PATENT DOCUMENTS

EP    1433744    6/2004
WO    0144796    6/2001
(Continued)

OTHER PUBLICATIONS

Gierhart, B. et al. C. Nanopore with transverse nanoelectrodes for electrical characterization and sequencing of DNA, Transducers '07, Proceedings of 14$^{th}$ International Conference on Solid-State Sensors, Actuators and Microsystems, Digest of Technical Papers, Lyon, France, Jun. 10-14, 2007. pp. 399-402.*

(Continued)

*Primary Examiner* — Roy King
*Assistant Examiner* — Xiaowei Su
(74) *Attorney, Agent, or Firm* — Theresa A. Lober

(57) ABSTRACT

In a process for fabricating a nanopore device, at least one carbon nanotube catalyst region is formed on a structure. A plurality of nanopores is formed in the structure at a distance from the catalyst region that is no greater than about an expected length for a carbon nanotube synthesized from the catalyst region. Then at least one carbon nanotube is synthesized from the catalyst region. This fabrication sequence enables the in situ synthesis of carbon nanotubes at the site of nanopores, whereby one or more nanotubes articulate one or more nanopores without requiring manual positioning of the nanotubes.

29 Claims, 4 Drawing Sheets

U.S. PATENT DOCUMENTS

| | | | |
|---|---|---|---|
| 6,350,488 | B1 | 2/2002 | Lee et al. |
| 6,361,861 | B2 | 3/2002 | Gao et al. |
| 6,515,339 | B2 | 2/2003 | Shin et al. |
| 6,528,020 | B1 | 3/2003 | Dai et al. |
| 6,555,362 | B2 | 4/2003 | Hidaka et al. |
| 6,566,704 | B2 | 5/2003 | Choi et al. |
| 6,566,983 | B2 | 5/2003 | Shin |
| 6,605,894 | B2 | 8/2003 | Choi et al. |
| 6,627,067 | B1 | 9/2003 | Branton et al. |
| 6,689,674 | B2 | 2/2004 | Zhang et al. |
| 6,706,402 | B2 | 3/2004 | Rueckes et al. |
| 6,706,566 | B2 | 3/2004 | Avouris et al. |
| 6,764,874 | B1 | 7/2004 | Zhang et al. |
| 6,919,592 | B2 | 7/2005 | Segal et al. |
| 6,942,921 | B2 | 9/2005 | Rueckes et al. |
| 7,120,047 | B2 | 10/2006 | Segal et al. |
| 7,253,434 | B2 | 8/2007 | Golovchenko et al. |
| 7,466,069 | B2 | 12/2008 | Golovchenko et al. |
| 7,468,271 | B2 | 12/2008 | Golovchenko et al. |
| 7,803,607 | B2 | 9/2010 | Branton et al. |
| 7,969,079 | B2 | 6/2011 | Golovchenko et al. |
| 8,092,697 | B2 * | 1/2012 | Branton et al. ............... 216/19 |
| 2001/0009693 | A1 | 7/2001 | Lee et al. |
| 2002/0014667 | A1 | 2/2002 | Shin et al. |
| 2002/0167374 | A1 | 11/2002 | Hunt et al. |
| 2002/0172767 | A1 | 11/2002 | Grigorian et al. |
| 2003/0173206 | A1 | 9/2003 | Delaunay et al. |
| 2003/0186167 | A1 | 10/2003 | Johnson, Jr. et al. |
| 2004/0043527 | A1 | 3/2004 | Bradley et al. |
| 2004/0200734 | A1 | 10/2004 | Co et al. |
| 2005/0224778 | A1 | 10/2005 | Dubin et al. |
| 2006/0065887 | A1 | 3/2006 | Tiano et al. |
| 2006/0158760 | A1 | 7/2006 | Portico Ambrosio et al. |
| 2007/0178507 | A1 | 8/2007 | Wu et al. |
| 2011/0155574 | A1 | 6/2011 | Golovchenko et al. |
| 2012/0234679 | A1 | 9/2012 | Garaj et al. |

FOREIGN PATENT DOCUMENTS

| | | |
|---|---|---|
| WO | 2004035211 | 4/2004 |
| WO | 2007084163 | 7/2007 |

OTHER PUBLICATIONS

Lagerqvist, J. et al. Influence of the environment and probes on rapid DNA sequencing via transverse electronic transport. Biophysical Journal. vol. 93 (Oct. 1, 2007), pp. 2384-2390. Published online on May 25, 2007.*

Peng et al. Patterned growth of single-walled carbon nanotube arrays from a vapor-deposited Fe catalyst. Applied Physics Letters. vol. 83, (Nov. 17, 2003), pp. 4238-4240.*

Postma, H. W. C. et al., Manipulation and imaging of individual single-walled carbon nanotubes with an atomic force microscope. Advanced Materials, Research News, vol. 17, (Sep. 2000), pp. 1299-1302.*

Chen, P. et al. Atomic layer deposition to fine-tune the surface properties and diameters of fabricated nanopores, Nano Letters, vol. 4, (2004), pp. 1333-1337.*

Yuzvinsky, T. D., et al. Precision cutting of nanotubes with a low-energy electron beam, Applied Physics Letters, vol. 86 (2005), pp. 053109.*

PCT/US2008/011412, International Search Report, WIPO publication first page, PCT/ISA/210 second sheet pp. 1-2, and patent family annex page, Dec. 2009.

PCT/US2008/011412, International Preliminary Report on Patentability, PCT/IB/373, PCT/ISA/237 cover sheet: pp. 1-3, and Separate sheet: sheets 1-2, Apr. 2010.

European Patent Application No. 08835267.9-1528, EP Examiner Communication, pp. 1-2, May 12, 2010.

European Patent Application No. 08835267.9-1528, Response to EP Examiner Communication, pp. 1-5, Clean Claim listing, pp. 1-3, marked up claim listing, pp. 1-5, Jun. 2010.

Homma et al., "Growth of suspended carbon nanotube networks on 100-nm-scale silicon pillars," Appl. Phys. Letts., vol. 81, No. 12, pp. 2261-2263, Sep. 2002.

Franklin et al., "Integration of suspended carbon nanotube arrays into electronic devices and electromechanical systems," Appl Phys. Letts., vol. 81, No. 5, pp. 913-915, Jul. 2002.

New Zealand Patent appl. No. 584570, Examiner Report, p. 1, Dec. 2010.

Cassell et al., "Directed Growth of Free-Standing Single-Walled Carbon Nanotubes," J. Am. Chem. Soc., vol. 121, pp. 7975-7976, Aug. 1999.

Fan et al., "Self-Oriented Regular Arrays of Carbon Nanotubes and Their Field EmissionProperties," Science, vol. 283, pp. 512-514, Jan. 1999.

Kong et al., "Synthesis of individual single-walled carbon nanotubes on patterned silicon wafers," Nature, vol. 395, pp. 878-881, Oct. 1998.

Martel et al., "Single- and multi-wall carbon nanotube field-effect transistors," Appl. Phys. Letts., vol. 73, No. 17, pp. 2447-2449, Oct. 1998.

Marty et al., "Self-assembled single wall carbon nanotube field effect transistors," IEEE Nano, vol. 2, pp. 240-243, Aug. 2003.

Peng et al, "Coulomb blockade in suspended $Si_3N_4$-coated single-walled carbon nanotubes," Appl. Phys. Letts., vol. 84, No. 26, pp. 5428-5430, Jun. 2004.

Peng et al., "Room-temperature single charge sensitivity in carbon nanotube field-effect transistors," Appl. Phys. Letts., vol. 89, pp. 243502-1-245502-3, Dec. 2006.

Walters et al., "Elastic strain of freely suspended single-wall carbon nanotube ropes," Appl. Phys. Letts., vol. 74, No. 25, pp. 3803-3805, Jun. 1999.

Zhang et al, "Metal coating on suspended carbon nanotubes and its implication to metal-tube interaction," Chem. Phys. Letts., vol. 331, pp. 35-41, Nov. 2000.

Zhang et al., "Electric-field-directed growth of aligned single-walled carbon nanotubes," Appl. Phys. Letts., vol. 79, No. 19, pp. 3155-3157, Nov. 2001.

Ren et al., "Growth of freestanding multiwall carbon nanotube on each nanonickel dot," Appl. Phys. Letts., vol. 75, No. 8, pp. 1086-1088, Aug. 1999.

Graham et al., "Towards the integration of carbon nanotubes in microelectronics," Diamond and Related Materials, vol. 13, Issue 4-8, pp. 1296-1300, 2004.

Chung et al., "Nanoscale gap fabrication and integration of carbon nanotubes by micromachining," Sensors and Actuators A, vol. 104, pp. 229-235, May 2003.

* cited by examiner

CARBON NANOTUBE SYNTHESIS FOR NANOPORE DEVICES

RELATED APPLICATIONS

This application claims the benefit of U.S. Provisional Application No. 60/997,297, filed Oct. 2, 2007, the entirety of which is hereby incorporated by reference.

STATEMENT REGARDING FEDERALLY SPONSORED RESEARCH

This invention was made with Government support under Contract No. 5RO1HG003703, awarded by NIH. The Government has certain rights in the invention.

BACKGROUND OF INVENTION

This invention relates generally to nanotubes, and more particularly relates to nanopore-based devices that incorporate nanotubes.

Nanopore-based devices have become important for a wide range of applications including detection, analysis, and quantification of species on the nanoscale. Nanopores are generally considered to be apertures having a diameter on the nanoscale. Many nanopore-based structures are being developed specifically for applications related to molecular sensing. For example, it has been suggested to translocate a molecule provided in an ionic solution, such as a strand of DNA, through a nanopore in a solid-state membrane, and to measure the blockage of ionic current through the nanopore as the molecule translocates through the nanopore.

It has been demonstrated that a characteristic blockage of the ionic solution, and the corresponding ionic current, through a nanopore can be attributed to a corresponding translocating molecule. But although molecule-specific ionic current blockage has been demonstrated, it has been found that the small differences in ionic current blockage corresponding to translocation of molecular components, such as different DNA bases, are generally beyond the resolution limit of conventional current amplifiers because, e.g., the intrinsic noise due to the electrically charged DNA bases is so large. It therefore is not in general currently possible to discriminate between specific DNA bases solely by measurement of ionic current blockage through a nanopore.

To overcome this limitation in discrimination between distinct translocating species, it has been proposed to alternatively, or to in addition, employ an electronic sensing arrangement, or electronic sensor, such as a tunneling junction, at the site of a nanopore, for electronically sensing molecules translocating through the nanopore. In one proposed configuration, there is provided one or more electrodes at the site of a nanopore to measure an electrical signal parameter indicative of molecular interaction with the nanopore. For example, a measurement can be made of transverse electronic current across a molecule translocating through a nanopore. This measurement technique is motivated by an analogy with scanning electron microscopy (STM) experiments, in which individual DNA bases are known to produce distinct electronic tunneling signals.

Theoretical calculations of a coupling interaction between a DNA molecule and embedded electrodes at the site of a nanopore have predicted orders of magnitude differences between the electronic tunneling currents corresponding to the four different DNA bases. To achieve such enhanced tunneling current sensing, it has been proposed to employ one or more carbon nanotubes as electrodes provided at the site of a nanopore. The unique electronic structure, exceptional elastic properties, and extremely high aspect ratio all characteristic of carbon nanotubes address many considerations for successfully implementing nanoscale electrodes at the site of a nanopore.

SUMMARY OF THE INVENTION

The invention provides nanopore geometries and corresponding fabrication processes for producing one or more carbon nanotubes at a selected nanopore device site. In one example process provided by the invention for fabricating a nanopore device, at least one carbon nanotube catalyst region is formed on a structure. A plurality of nanopores is formed in the structure at a distance from the catalyst region that is no greater than about an expected length for a carbon nanotube synthesized from the catalyst region. Then at least one carbon nanotube is synthesized from the catalyst region.

This fabrication sequence enables the in situ synthesis of carbon nanotubes at the site of nanopores, whereby one or more nanotubes articulate one or more nanopores without requiring manual positioning of the nanotubes. This process is adaptable to a wide range of structures and nanopore device configurations, enabling the realization of nanopore devices with batch microfabrication technology. Other features and advantages of the invention will be apparent from the following description and accompanying figures, and from the claims.

DETAILED DESCRIPTION OF THE INVENTION

Figure 1A:
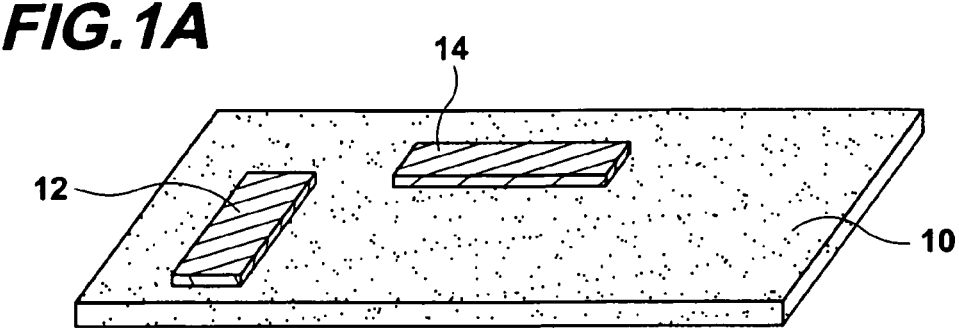
FIGS. 1A-1B are perspective schematic views of example fabrication process steps provided by the invention for producing a nanotube at a nanopore, illustrating a first example configuration of carbon nanotube catalyst regions at a nanopore array.
Figure 1B:
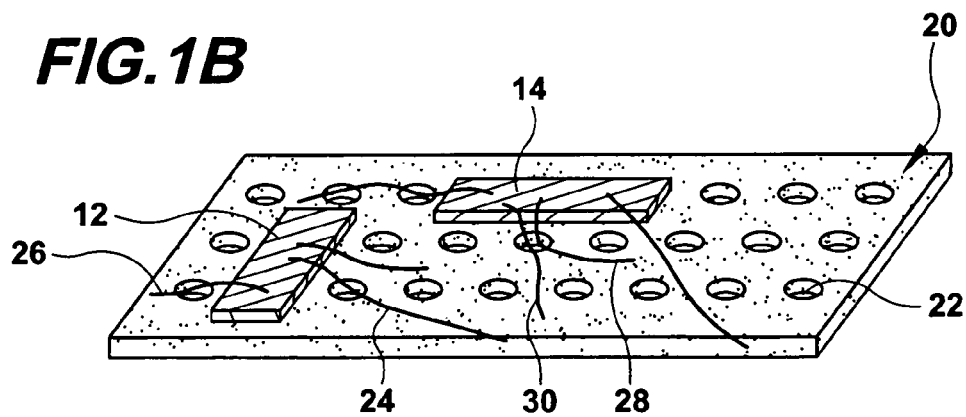

Referring to FIGS. 1A-1B, process steps for producing one or more nanopores articulated with carbon nanotubes are schematically shown. Each process step and various alternative processes and configurations will be described in detail below. As an introductory description, in general, in a first process step, there is provided a structure 10 in which it is desired to achieve one or more nanopores articulated with one or more carbon nanotubes. As explained below, the structure 10 can be provided as any material and geometry that is suitable for an intended nanopore device application. On a surface of the structure 10 there are provided one or more carbon nanotube catalyst regions 12, 14, of a selected material and geometry for carbon nanotube synthesis, as described below.

Referring to FIG. 1B, one or more arrays 20 of nanopores 22 are formed in the structure 10 in the vicinity of the catalyst regions 12, 14. Each nanopore array includes at least two nanopores, preferably more, and are located such that the probability of synthesis of one or more carbon nanotubes across at least one nanopore is maximized. This probability is maximized by forming the nanopores at a distance that is no greater than an expected carbon nanotube length, e.g., no greater than about 20 microns from the location of the catalyst regions. The nanotube catalyst regions 12, 14 are then exposed to selected carbon nanotube synthesis conditions to grow carbon nanotubes. As shown in FIG. 1B, during this synthesis, one or more carbon nanotubes 24, 26, 28, 30 grow across the nanopore array and cross the diameter or at the edge of one or more nanopores.

Figure 2A:
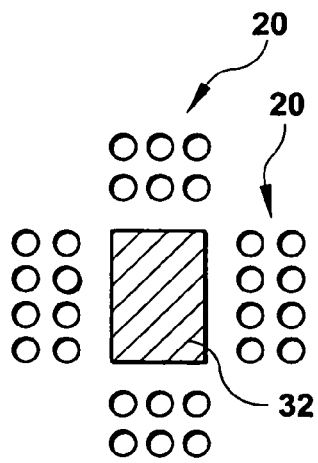
FIGS. 2A-2B are planar schematic views of two additional example configurations of carbon nanotube catalyst regions provided at one or more nanopore arrays.
Figure 2B:
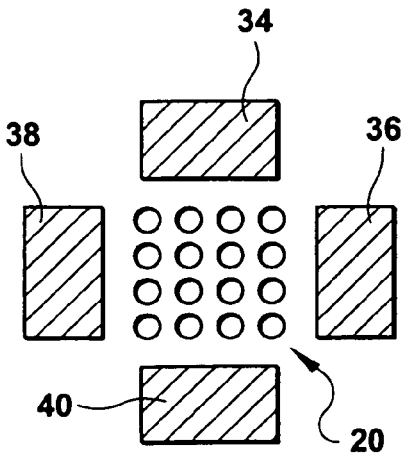

To maximize the likelihood of carbon nanotube growth across a nanopore, a plurality of nanotube catalyst regions can be employed and preferably are positioned at sites in the vicinity of one or more nanopore arrays. For example, as shown in FIGS. 2A-2B, one carbon nanotube catalyst region 32 can be positioned centrally to a plurality of nanopore arrays 20 that are disposed at the periphery of the catalyst region. Alternatively, one nanopore array 20 can be provided centrally to a plurality of catalyst regions 34, 36, 38, 40. In accordance with the invention, no particular arrangement of catalyst regions and nanopore arrays is required; but at least one nanotube catalyst region is provided in the vicinity of a plurality of nanopores that can be arranged with regular spacing, as in an array, or in a non-regular spacing of a grouping of nanopores.

This fabrication sequence, as described generally above, enables the in situ synthesis of carbon nanotubes at the site of nanopores, whereby one or more nanotubes articulate one or more nanopores without manual positioning of the nanotubes. This process is adaptable to a wide range of structures and nanopore device configurations, enabling the realization of nanopore devices with batch microfabrication technology.

Considering now one example implementation of the nanotube synthesis process of the invention, for many applications it can be particularly useful to provide a nanopore in a solid state structure that is formed as a membrane. The term "membrane" here refers to a thin layer of material that is self-supported across its extent and is supported at its edges by, e.g., a substrate frame or other supporting structure. A nanopore provided in such membrane, particularly a membrane of micro- or nano-scale thickness, is important for enabling molecular detection and analysis techniques such as DNA sequencing.

Figure 3A:
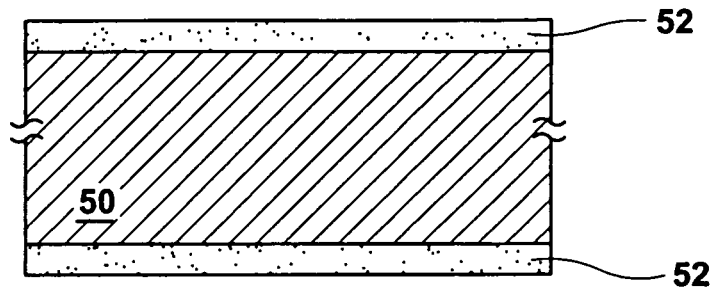
FIGS. 3A-3E are schematic views of example fabrication process steps in a fabrication sequence provided by the invention for producing a nanotube-articulated nanopore device in a membrane structure.

Referring to FIG. 3A, in an example fabrication sequence for producing nanotube-articulated nanopores in a membrane, there is provided a substrate, e.g., a microelectronic substrate such as a silicon substrate 50. A layer 52 of a selected membrane material, e.g., $SiN_x$, is deposited on the substrate. In the conventional manner, the membrane material is formed on both the front and backside of the substrate. The membrane can be formed of multiple materials, e.g., $SiN_x$ and $SiO_2$, or other combination of materials, and can be electrically insulating, conducting, or semiconducting, as-required for a given application. The thickness of the membrane material is selected to minimize breakage when in use. For example, a $SiN_x$ membrane material of between about 50 nm-about 5 μm can be suitable for many applications. After membrane layer deposition, the membrane material can be processed, e.g., by annealing or cleaning. For example, a $SiN_x$ membrane can be cleaned in TCE, acetone, and methanol, and baked at a temperature of, e.g., about 150° C. Other membrane material processing steps can further be carried out as-required for a given application.

The membrane material on the substrate backside is then patterned to expose the substrate through a window in the membrane material layer, and the substrate is etched, or bulk micromachined, to remove the unmasked substrate material in the window and expose the membrane material at the front side of the substrate. For example, a silicon substrate can be anisotropically etched, e.g., with KOH or other etchant, to remove the silicon and produce a $SiN_x$ membrane 54 that is free-standing. The membrane geometry can be generally rectangular, extending for, e.g., 100 μm×100 μm, or other geometry, supported only at its edges by the peripheral silicon substrate 50, now forming a frame around the membrane.

Figure 3B:
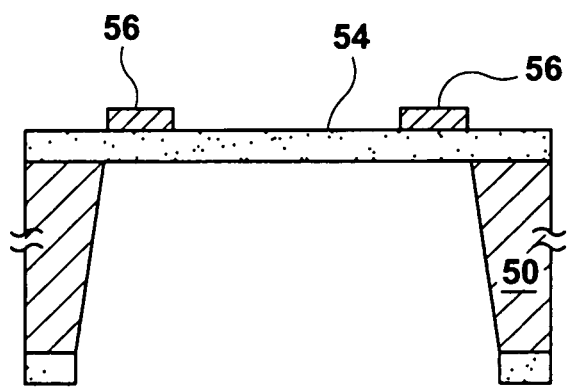

Also as shown in FIG. 3B, carbon nanotube catalyst regions 56 can at this point be formed on the membrane. In one example process, an intermediate dielectric layer, e.g., $Al_2O_3$, can be first deposited to prevent diffusion of the catalyst material and to optimize the catalytic action. Electron beam evaporation, atomic layer deposition, or other suitable process, can here be employed to form the $Al_2O_3$ layer and then to form the catalyst layer. Iron or other suitable catalyst material can be employed.

With electron beam evaporation, a precise layering of the alumina and Fe or other catalyst material can be achieved, e.g., with a 5 nm-thick layer of alumina and a layer of Fe having a thickness of between about 0.5 nm-1 nm, evaporated at a pressure of, e.g., about $3-5 \times 10^{-7}$ Torr. In one example process, Poly(methyl methacrylate) (PMMA) resist can be patterned on the catalyst layer, and electron beam lithography (EBL) patterning, with, e.g., a Raith-150 system, and lift-off with acetone, to form the catalyst regions. The invention is not limited to a particular catalyst region formation process; photolithography, self-assembly, or other selected process can be employed to produce catalyst regions. The resulting catalyst regions 56 are positioned on or near to the membrane in an arrangement corresponding to an intended location of one or more nanopore devices. For many applications, a catalyst region of, e.g., about $1 \times 1$ μm$^2$, can provide sufficient catalyst extent.

At this point in the process, one or more arrays of pores, or apertures, can be formed in the membrane. If the pores have a diameter on the micro- or nano-scale, the pores are herein referred to as nanopores. It is recognized that the pores can be formed as holes, channels, or other vias having a geometry that extends through the full thickness of the membrane. For clarity in the instant example, the holes are referred to as nanopores. In accordance with the invention, at least two nanopores are formed in the membrane in the vicinity of the one or more catalyst regions.

For many applications, the membrane thickness as-formed may be greater than optimal to achieve a desired nanopore device performance. For example, a $SiN_x$ membrane layer thickness of 250 nm-300 nm may be so great as to result in a low ionic conductivity of an ionic solution translocating through the length of a nanopore in the membrane. In accordance with the invention, this condition can be remedied by providing one or more thinned regions of the membrane at which arrays of pores are to be formed. This membrane thinning process, if desired, can be incorporated into the nanopore formation step.

Figure 3C:
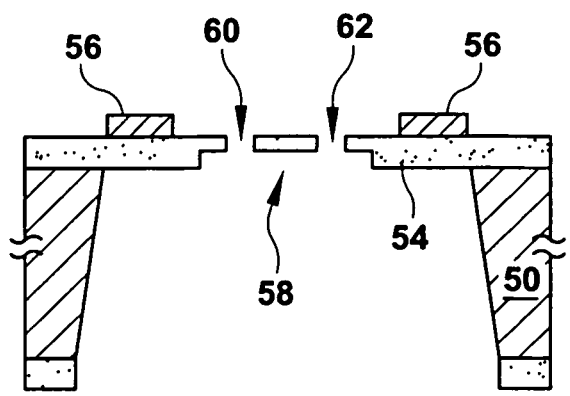

As shown in FIG. 3C, in such a process step, a focused ion beam, or other suitable energetic species, is directed at the back of the substrate to both thin the membrane 54 and to form nanopores 60, 62 in the thinned membrane region 58. The features shown in FIG. 3C are far out of scale to illustrate all features in one view. In one example process, a 50 KV Ga$^+$ focused ion beam (FIB), e.g., a FEI Micrion 9600 FIB system, is directed at the backside of the membrane 54, with settings of, e.g., about 1.4 pA beam current and 15 μm aperture diameter. To minimize the diameter of the nanopores formed by the FIB, it can be preferred to operate the FIB in single-pixel mode, wherein the ion beam is maintained at a single point, i.e., pixel, for a selected dwell time and then shifted to an adjacent selected point at a distance much larger than the ion beam diameter, which is about 10 nm in this example system. This operation is in contrast to a more standard operating FIB mode wherein the ion beam is continuously scanned between selected points. With an ion beam dwell time of between about 5 s-7 s, nanopores having diameters of, e.g., between about 20 nm-about 60 nm can be formed, with a spacing of, e.g., between about 100 nm-about 200 nm between the nanopores. In general, it can be preferred in accordance with the invention to produce nanopores less than about 1 micron in diameter, and more preferably no greater than about 100 nm in diameter. FIG. 3C illustrates two such nanopores 60, 62. Arrays of tens or hundreds of such nanopores can be formed in this manner, at distances of, e.g., several microns, e.g., less than about 20 microns, more preferably less than about 5 microns, from the carbon nanotube catalyst regions 56. In general, the distance from a nanotube catalyst region to a location at which the nanopores are to be formed is preferably no greater than the expected length for a carbon nanotube synthesized from that catalyst region.

Prior to the nanopore formation, or between each nanopore milling, the membrane 54 can be thinned with the ion beam or other energetic species. In the example of FIG. 3C the thinned membrane region 58 includes a plurality of nanopores. Alternatively, the membrane can be thinned, e.g., in a 150×150 nm square area, in which only a single nanopore is to be provided. In this case the nanopore can be milled through, e.g., the center of a thinned region just after that region is thinned, and then the ion beam moved to a next region to be thinned and provided with a nanopore. At the completion of the process, an array of nanopores is formed in the vicinity of the carbon nanotube catalyst regions.

With the nanopore array complete, the structure is exposed to carbon nanotube growth conditions to synthesize one or more carbon nanotubes in place at the nanopore array. Chemical vapor deposition (CVD) conditions or other selected conditions can be employed to synthesize the carbon nanotubes. In one example process, CVD synthesis of single-walled carbon nanotubes is carried out, e.g., in a 1 inch-diameter tube furnace with methane gas ($CH_4$) employed as the carbon source. In one example CVD process, the structure is loaded into the furnace and thermally ramped to a temperature of about 900° C. in a flow of 500 sccm Ar. At the temperature of 900° C. the structure is annealed, e.g., in a 200 sccm flow of $H_2$ for 10 minutes. The carbon nanotube growth is then conducted by introducing 1000 sccm $CH_4$ for about 15 minutes. After this growth step, the system is cooled to ambient temperature in 500 sccm Ar flow.

Figure 3D:
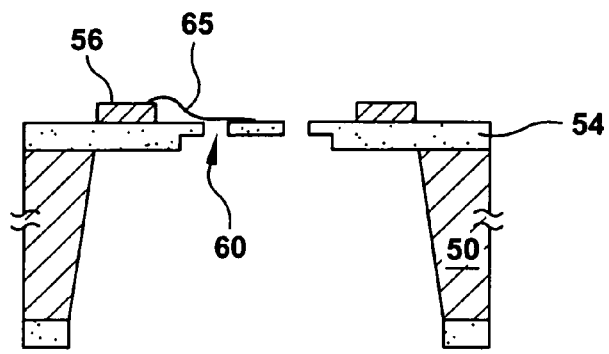

This growth process can be employed to produce single-walled carbon nanotubes (SWNT) that extend for at least several microns in length, and can extend for 20 μm or more in length. It is understood in accordance with the invention that as a carbon nanotube grows from a catalyst region, the nanotube tends to flop across the substrate, and in doing so, given the proximity of nanopores to the catalyst region, the nanotube comes to rest across a nanopore, at a perimeter of a nanopore, or adjacent or near to a nanopore. Referring to FIG. 3D an example of this SWNT growth result is shown, in which a carbon nanotube 65 has been synthesized from a catalyst region 56 and extends across the substrate over a nanopore 60.

Using atomic force microscopy (AFM) or other selected imaging, the nanopore array is viewed after nanotube growth to identify and select a nanotube that has grown across, at a perimeter, or adjacent to a nanopore. It can be helpful to provide AFM alignment marks within the AFM field of view of the nanopores to enable determination of the location of a selected nanotube. For many applications, AFM imaging can be preferred to avoid contamination or defect formation that could result from electron beam imaging.

In accordance with the invention, as the AFM investigation of the nanopore array is carried out, the AFM tip can be employed to move a synthesize carbon nanotube to a selected location at a nanopore in the array. A carbon nanotube that is near to but not perfectly positioned at a selected nanopore can be precisely positioned at the selected nanopore by the AFM tip. Thus, if no carbon nanotube came to rest at a nanopore during nanotube synthesis, a selected nanotube can be guided to one of the nanopores with the AFM tip. Because the nanopores are formed as an array, it can be expected that one of the synthesized carbon nanotubes is close to a nanopore if not directly sited at a nanopore. Accordingly, it can be expected that only a small repositioning of a nanotube, if any, may be required to achieve alignment of one of the synthesized nanotubes with one of the nanopores. Alignment of a nanotube with a nanopore can be at a periphery of a nanopore, across the open diameter of a nanopore, near to a nanopore, or in another configuration relative to a nanopore as-required for a given application.

Figure 3E:
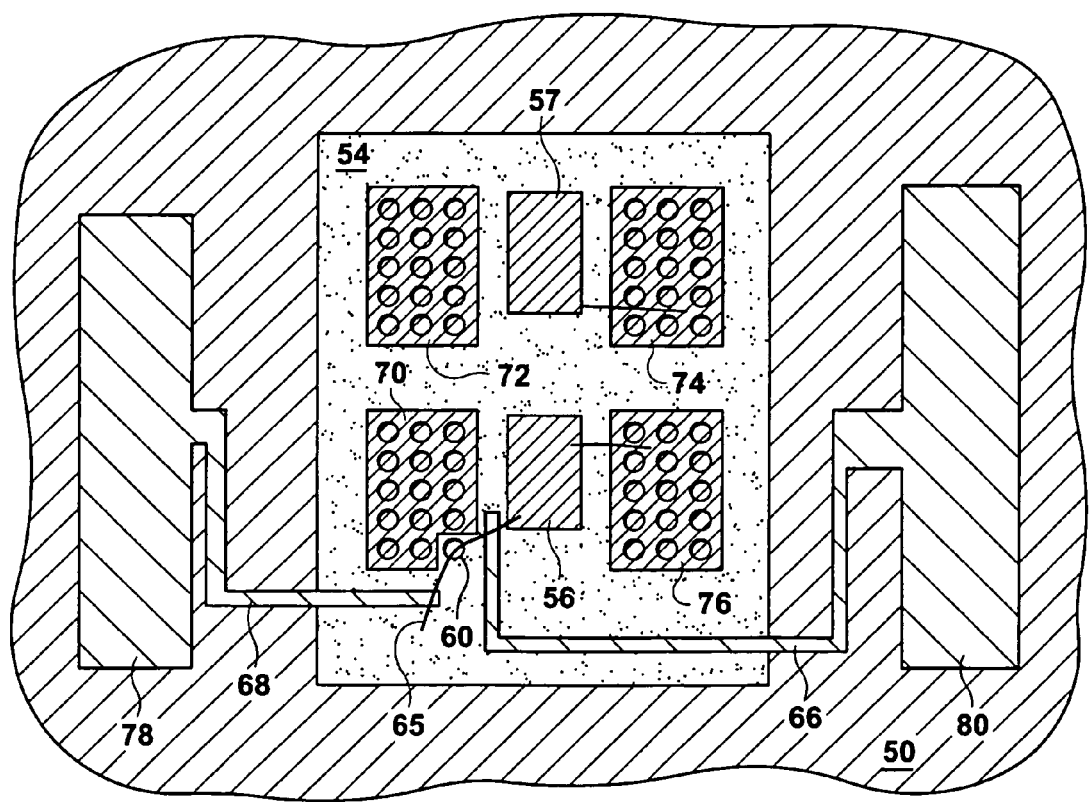

Once a nanopore that is articulated with a carbon nanotube has been provided in a selected configuration, that nanopore is configured for device operation. Referring to FIG. 3E, in one example of such, a nanopore 60 having a nanotube 65 disposed across the nanopore 60 is selected for device operation. The nanotube 60 grew from a catalyst region 56 provided in the vicinity of nanopore arrays 70, 72, 74, 76, here along with a second catalyst region 57, on a membrane 54 supported at its periphery by a substrate 50 in the manner described above.

In a next process step, electrical contacts 66, 68 are made to the nanotube 65 on each side of the selected nanopore 60. The electrical contacts 66, 68 are in turn connected to large contact pads 78, 80 for making contact with external electrical probes. The metal deposition employed for making electrical contacts to the nanotube 65 can also be employed to cover and therefore close up the nanopores that are not to be configured for device operation. For example, as shown in FIG. 3E, layers of metal can be provided over those nanopores in the nanopore arrays 72, 74, 76 for which no nanopores are to be employed as devices, as well as the unused nanopores in the nanopore array 70 in which one or more selected nanopores are to be employed as devices. With this metal deposition complete, there is produced an operable nanopore 60 articulated with a nanotube 65 and having electrical contacts 66, 68 to external probe pads, with the remaining unused nanopores covered.

In accordance with the invention, it is recognized that in forming a conductive metal layer in contact with a selected nanotube, the integrity of the nanopore of interest must be maintained by prohibiting clogging of the nanopore, and the integrity of the nanotube of interest must be maintained by prohibiting the formation of residue or defects on the nanotube. During conventional lithographic processing, resist developer or lift-off solvent can sweep up and concentrate trace impurities and deposit such in a nanopore that is exposed to a receding liquid meniscus. Further, a carbon nanotube can make a composite with a lithographic polymer material, such as PMMA, and it can be difficult to completely remove such without a high-temperature heat treatment. PMMA contamination on the surface of a nanotube can serve as a deposition site for subsequent material formation processes employed to tailor the nanopore properties, as described below.

It is therefore preferred in accordance with the invention, in the process of forming lithographic patterns for metal deposition, to avoid the use of electron beam resists such as PMMA and instead to employ methylmethacrylate/methacrylate acid copolymer (MMA-MAA) as a resist material, and to employ dichloroethylene (DCE) as a lift-off solvent. It can further be preferred to protect the underside of the substrate and membrane from exposure to polymer developer by mounting the device structure on a handle wafer or chip in the conventional manner. Meticulous cleaning and repeated rinsing steps during lift-off removal are further preferred. The lift-off process is preferably completed by critical-point drying rather than air drying to prevent a receding meniscus. Thus, in accordance with the invention, MMA-MAA is preferably employed in an electron beam lithographic patterning step with careful rinsing and drying to delineate windows in the resist where metal is to be deposited to form contact pads and connections and to cover over unwanted nanopores.

Once the lithographic patterning is complete, one or more metal layers are then deposited to form the nanotube contacts and nanopore cover regions, and a lift-off process is completed. In selection of the metal contact material, it is understood that while Pd is known to make a good ohmic contact to carbon nanotubes, Pd does not form a strong native oxide on a carbon nanotube to prevent current leakage from the underlying carbon nanotube to a surrounding environment. The native oxide of Pd also does not serve as a good surface for atomic layer deposition (ALD) of additional layers, such as dielectric layers, over the contacts. It therefore can be preferred in accordance with the invention to employ a layer of Pd with an overlayer of another metal, a metal oxide, or an oxide. If a metal is to be used, Mo can be preferred because unlike Al or Ti, Mo exhibits only very low atomic diffusion into Pd, and no alloying generally occurs. Further, metal oxides such as $Al_2O_3$ can be readily deposited on Mo by atomic layer deposition (ALD). A contact region formed of Pd and Mo exhibit very low contact resistance to a nanotube, e.g., <10 k$\Omega$, and very low leakage current in an electrolyte solution, e.g., ~10 pA at 200 mV in 1M KCl. Therefore, an electrical contact layer of Pd and Mo can be preferred for many applications, with a Pd layer thickness of, e.g., about 15 nm a Mo layer thickness of, e.g., about 15 nm. The metal layers can be evaporated in the conventional manner. Alternatively, or in addition, a layer of metal oxide or oxide can be provided over the metal; e.g., a layer of $Al_2O_3$ or $SiO_2$ can be employed over the Pd layer.

Following metal evaporation, a lift-off process is executed with great care to ensure that no resist material is left on the nanotube or the selected nanopore over which it spans. In one example lift-off process, the structure is subjected first to three 10 minute-long warm TCE baths with mechanical agitation and syringing as beakers are changed. Then two heated baths in DCE are completed, followed by transfer to methane, which is removed by critical-point drying. An unclogged, contamination-free nanotube-articulated nanopore device is thusly produced. At this point, electrical connection can be made to the ends of the selected carbon nanotube to electrically characterize the nanotube, e.g., as metallic or semiconducting, and to determine the leakage current to be expected.

The invention is not limited to this metal deposition and lift-off process. Alternative deposition and patterning processes can be employed as-suited for a given application. For example, water-based ice lithography can be employed for a metal lift-off process, as described in U.S. Patent Application Publication No. US2007/0262050, by Golovchenko et al., published Nov. 15, 2007, the entirely of which is hereby incorporated by reference; and in U.S. Patent Application Publication No. US2007/0128357, by Branton et al., published Jun. 7, 2007, the entirely of which is hereby incorporated by reference. In such a process, water or other vapor is condensed directly to the solid phase to form a resist that can be patterned by, e.g., electron beam, and after metal deposition, the resist is sublimated or otherwise vaporized from the solid phase directly to the vapor phase. This process entirely eliminates liquid conditions that can cause contamination and clogging. Other such lithographic patterning and lift-off processing can be employed in a suitable manner for maintaining the integrity of a nanotube-articulated nanopore device as electrical contacts are made to the device.

In a next process step, the electrical contacts and probe pads for the nanopore device are protected by an electrically insulating layer. The coating employed for this electrically insulating layer can be employed in the same process step to partially fill the nanopore to reduce the diameter of the nanopore in a well-controlled manner that achieves a selected nanopore diameter. One well-suited process for achieving this nanopore diameter reduction is the ALD process described above, applied to a nanopore in the manner described in U.S. Patent Application Publication No. US2005/0241933, by Branton et al., published Nov. 3, 2005, the entirely of which is hereby incorporated by reference; and as applied to a nanotube-articulated nanopore in the manner described in U.S. Patent Application Publication No. US2008/0171316, by Branton et al., published Jul. 17, 2008, the entirely of which is hereby incorporated by reference.

Such an ALD process is particularly well-suited here because the deposition of material by ALD is strictly dependent on the chemical interaction between a gas-phase molecule and hydroxyl or other functional groups accessible at the surface of the material on which a coating is to be deposited. Absent such functional groups, no deposition of the gas-phase molecules occurs. Carbon nanotubes as-synthesized do not in general possess functionalized surfaces that provide the requisite hydroxyl or other functional groups for deposition of the gas phase material. Thus, if an insulating material such as aluminum oxide or hafnium oxide is deposited by ALD on a device configuration that includes silicon, silicon nitride and nanotubes, or metals, aluminum oxide or hafnium oxide will grow uniformly by chemical reaction at the surfaces of all of these structures, including the newly formed aluminum oxide or hafnium oxide surfaces, but will not grow from the carbon nanotube surfaces which, as grown, do not have functional groups such as hydroxyl groups at their surface. This condition can be exploited to enable site-specific deposition of such materials on the support structure but not directly on, from, or over the unsupported nanotube, e.g., not on or over a region of a nanotube that is suspended over a nanopore.

Figure 4:
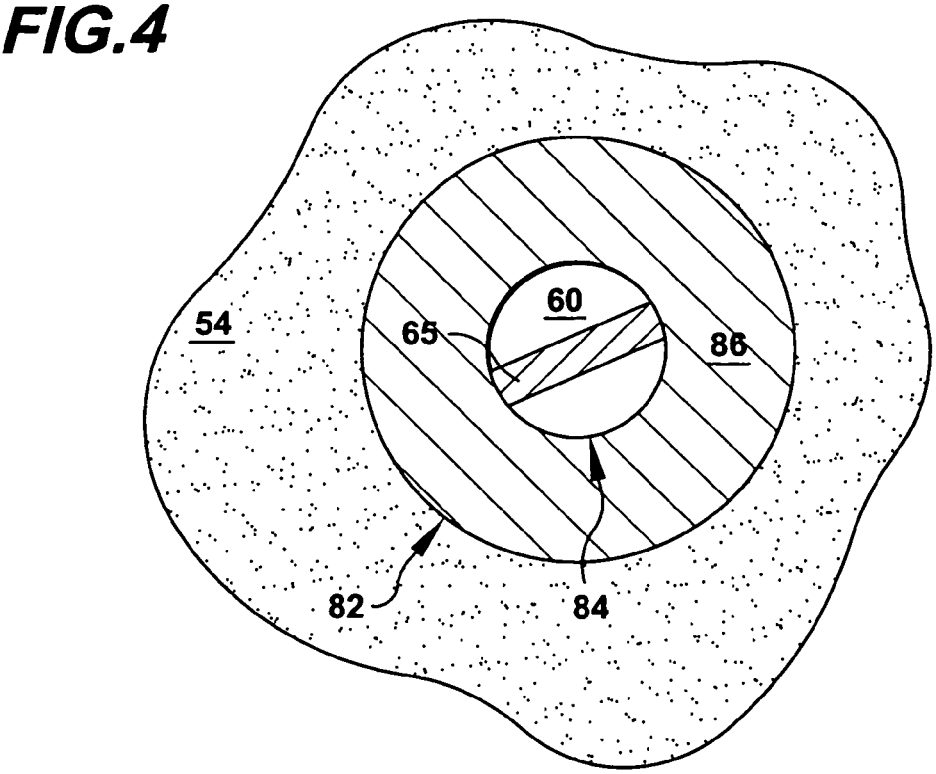
FIG. 4 is a planar schematic view of a nanotube-articulated nanopore provided by the invention after fine tuning of the nanopore diameter with ALD.

In one such scenario, a selected number of ALD cycles are carried out, depositing material on all surfaces of the membrane and electrodes, and including the walls of the nanopore. The deposition of the selected material extends over and may cover regions of the nanotube that are supported by, or proximal to any of the silicon nitride or newly grown ALD material, but does not itself originate from the nanotube surface. As the material deposition is continued, the build up of deposited material at the nanopore reduces the extent of the nanopore. As shown in FIG. 4, the deposition process can be continued until an initial nanopore perimeter 82 is reduced to a selected final nanopore diameter 84, with the deposited material 86 filling the region between the original and final nanopore perimeter.

Due to the very precise nature of the ALD process, the material thickness produced by each ALD cycle can be precisely characterized for a given nanopore and nanotube arrangement and dimensions and controlled to achieve a selected final nanopore diameter with the upper side of the nanotube coated. For example, with a starting aperture of 50 nm, 220 ALD cycles, each adding a layer 1 Å-thick of $Al_2O_3$, by alternating cycles between trimethylaluminum (TME) and water vapor flow and purge, produces a final pore of 6 nm in diameter. Thus, the nanopore diameter can be very precisely fine tuned with an ALD process to produce a desired nanopore structure.

The ALD process also deposits material on the membrane and electrical contacts, whereby the nanopore device and electronics are insulated and passivated. As shown in FIG. 4, only the carbon nanotube 65 is uncoated, and therefore is maintained in a state for electrical sensing of a molecule or other species during interaction of that species with the nanopore during operation of a nanopore-based device.

Figure 5:
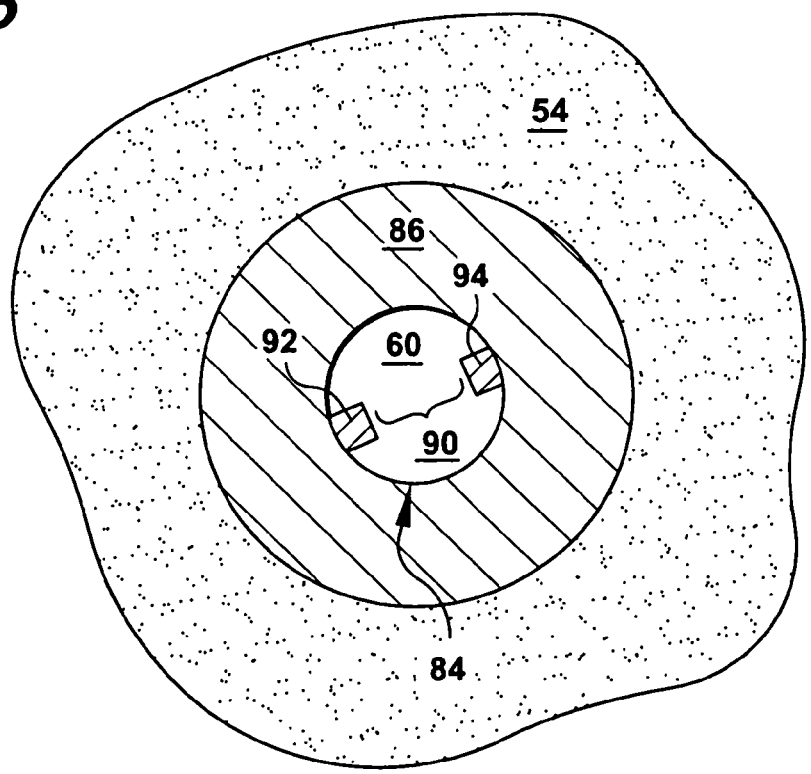
FIG. 5 is a planar schematic view of a nanotube-articulated nanopore provided by the invention after cutting the nanotube to form nanotube probes at the nanopore periphery.

If desired, subsequent processing can be conducted to further tailor the geometry of the nanotube-articulated nanopore. In one example process, the nanotube segment exposed across the diameter of the nanopore can be cut to produce two nanotube ends at opposite sides of the nanopore. Referring to FIG. 5, in this process, a tunneling gap, or other type of gap, 90 is formed between the two resulting nanotube probes 92, 94 sited at the nanopore perimeter 84. The nanotube probes 92, 94 can extend into the nanopore 60 or be sited to align with the edge of the nanopore.

These configurations and a process to produce such can be implemented in the manner described in U.S. Patent Application Publication No. US2008/0171316, by Branton et al., published Jul. 17, 2008, the entirely of which is hereby incorporated by reference. Here an electron beam, e.g., in a transmission electron microscope, can be employed, with the beam directed through the nanopore to cut the exposed nanotube and form cut nanotube edges at the nanopore perimeter. Low-energy Ar ion beam, $O_2$ plasma etching, reactive ion etching, and other etch techniques alternatively can be employed to cut the nanotube and form nanotube probes at the nanopore perimeter. Whatever etching process is employed, once complete, the nanopore is articulated with nanotube probe ends that are in alignment with the nanopore periphery.

With this description, a process for the in situ synthesis of carbon nanotubes at the site of a nanopore device is provided. A complete nanotube-articulated nanopore device, including electrical contacts, is produced in a reliable and reproducible manner that enables implementation of a wide range of nanopore-based sensing and analysis systems. It is recognized, of course, that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A method for fabricating a nanopore device comprising:
    forming at least one carbon nanotube catalyst region on a structure;
    forming a plurality of nanopores in the structure at a distance from the catalyst region that is no greater than an expected length for a carbon nanotube synthesized from the catalyst region, each nanopore having a diameter that is no greater than about 100 nm; and
    synthesizing at least one carbon nanotube from the catalyst region.

2. The method of claim 1 wherein the plurality of nanopores is formed in the structure at a distance from the catalyst region that is no greater than 20 microns.

3. The method of claim 1 wherein forming a plurality of nanopores comprises forming an array of nanopores.

4. The method of claim 1 wherein forming at least one carbon nanotube catalyst region comprises forming a plurality of catalyst regions.

5. The method of claim 4 wherein synthesizing at least one carbon nanotube comprises synthesizing a plurality of carbon nanotubes.

6. The method of claim 1 wherein forming a plurality of nanopores comprises forming an array of nanopores at a peripheral location around at least one catalyst region.

7. The method of claim 1 wherein forming a plurality of nanopores comprises forming an array of nanopores at a location central to peripheral catalyst regions.

8. The method of claim 1 wherein catalyst region formation comprises formation of a region of $Al_2O_3$ and formation of a region of metal catalyst comprising Fe on the $Al_2O_3$ region.

9. The method of claim 1 wherein synthesizing at least one carbon nanotube comprises vapor synthesis of at least one carbon nanotube.

10. The method of claim 1 further comprising identifying a synthesized carbon nanotube a portion of which is located at one of the plurality of nanopores.

11. The method of claim 10 wherein identifying a synthesized carbon nanotube comprises inspecting synthesized carbon nanotubes with an atomic force microscope.

12. The method of claim 10 wherein identifying a synthesized carbon nanotube at one of the nanopores comprises identifying a carbon nanotube a portion of which crosses one of the nanopores.

13. The method of claim 10 wherein identifying a synthesized carbon nanotube at one of the nanopores comprises identifying a carbon nanotube a portion of which is adjacent to one of the nanopores.

14. The method of claim 1 further comprising moving a synthesized carbon nanotube to a selected nanopore.

15. The method of claim 14 wherein moving a synthesized carbon nanotube comprises pushing a carbon nanotube with an atomic force microscope tip.

16. The method of claim 14 wherein moving a synthesized carbon nanotube comprises positioning a portion of the synthesized carbon nanotube across a selected nanopore.

17. The method of claim 1 wherein forming the plurality of nanopores comprises directing a focused ion beam at the structure at selected nanopore locations on the structure.

18. The method of claim 1 wherein forming the plurality of nanopores comprises thinning the structure at selected nanopore locations on the structure.

19. The method of claim 1 wherein the structure comprises a free-standing membrane supported at its edges by a substrate.

20. The method of claim 19 wherein the membrane comprises a $SiN_x$ membrane.

21. The method of claim 10 further comprising forming electrical contact regions on the identified nanotube on opposite sides of the corresponding nanopore at which a portion of the nanotube is located.

22. The method of claim 21 further comprising forming external electrical contact pads connected to the electrical contact regions.

23. The method of claim 10 further comprising identifying nanopores at which no synthesized carbon nanotubes are located and coating those identified nanopores.

24. The method of claim 23 wherein coating the identified nanopores at which no carbon nanotubes are located comprises forming a layer of material on the structure at the location of the identified nanopores.

25. The method of claim 10 further comprising coating a nanopore at which a synthesized carbon nanotube is identified to be located with a layer of material to produce a selected nanopore diameter.

26. The method of claim 25 wherein the nanopore coating comprises atomic layer deposition.

27. The method of claim 25 wherein the nanopore coating forms a layer of $Al_2O_3$.

28. The method of claim 10 further comprising cutting through a portion of the identified nanotube at a nanopore to form nanotube ends at peripheral nanopore locations.

29. The method of claim 28 wherein cutting through a portion of the identified nanotube comprises directing an electron beam at the nanotube portion.

* * * * *